(12) United States Patent
Van Kruchten et al.

(10) Patent No.: US 8,658,841 B2
(45) Date of Patent: *Feb. 25, 2014

(54) PROCESS FOR THE PREPARATION OF ALKYLENE GLYCOL

(75) Inventors: Eugene Marie Godfried Andre Van Kruchten, Amsterdam (NL); Dominicus Maria Rekers, Amsterdam (NL); Mathias Jozef Paul Slapak, Amsterdam (NL)

(73) Assignee: Shell Oil Company, Houston, TX (US)

( * ) Notice: Subject to any disclaimer, the term of this patent is extended or adjusted under 35 U.S.C. 154(b) by 1242 days.

This patent is subject to a terminal disclaimer.

(21) Appl. No.: 12/191,932

(22) Filed: Aug. 14, 2008

(65) Prior Publication Data

US 2009/0143627 A1    Jun. 4, 2009

(30) Foreign Application Priority Data

Aug. 14, 2007  (EP) .................................... 07114306

(51) Int. Cl.
  *C07C 33/035*    (2006.01)
(52) U.S. Cl.
  USPC ........................................................ 568/857
(58) Field of Classification Search
  USPC ........................................................ 568/857
  See application file for complete search history.

(56) References Cited

U.S. PATENT DOCUMENTS

| | | | | |
|---|---|---|---|---|
| 4,400,559 A * | 8/1983 | Bhise | ............................ | 568/858 |
| 4,822,926 A * | 4/1989 | Dye | ............................. | 568/867 |
| 4,831,196 A * | 5/1989 | Buonicore et al. | ............ | 568/867 |
| 5,218,135 A | 6/1993 | Buysch et al. | ................. | 558/277 |
| 5,763,691 A * | 6/1998 | Kawabe et al. | ............... | 568/867 |
| 6,080,897 A | 6/2000 | Kawabe | ........................ | 568/858 |
| 6,417,411 B2 * | 7/2002 | Kakimoto et al. | ............. | 568/867 |
| 8,063,256 B2 * | 11/2011 | Van Kruchten | ............... | 568/910 |
| 8,193,374 B2 * | 6/2012 | Evans et al. | .................... | 549/230 |
| 2003/0098281 A1 * | 5/2003 | Shutt et al. | ..................... | 210/663 |
| 2004/0175316 A1 * | 9/2004 | Bos et al. | .................... | 423/245.1 |
| 2008/0182999 A1 * | 7/2008 | Rekers et al. | .................. | 549/512 |

FOREIGN PATENT DOCUMENTS

| | | | | |
|---|---|---|---|---|
| CN | 1699359 | 11/2005 | ............ | C07D 317/38 |
| EP | 24628 | 3/1981 | ............ | C07C 301/32 |
| EP | 776890 | 6/1997 | ............ | C07D 317/38 |
| GB | 2107712 | 5/1983 | ............ | C07D 317/38 |

* cited by examiner

*Primary Examiner* — Johann R Richter
*Assistant Examiner* — Kofi Adzamli

(57) ABSTRACT

The invention provides a process for the preparation of an alkylene glycol from an alkene. A gas composition from an alkylene oxide reactor is supplied to an alkylene oxide absorber comprising a column of vertically stacked trays or comprising a packed column. Lean absorbent comprising at least 20 wt % water is supplied to the alkylene oxide absorber and is contacted with the gas composition in the presence of one or more catalysts that promote carboxylation and hydrolysis. At least 50% of the alkylene oxide entering the alkylene oxide absorber is converted in the alkylene oxide absorber. Fat absorbent is withdrawn from the absorber, is optionally supplied to finishing reactors and/or a flash vessel or light ends stripper, and is subsequently subjected to dehydration and purification to provide a purified alkylene glycol product stream.

17 Claims, 6 Drawing Sheets

PROCESS FOR THE PREPARATION OF ALKYLENE GLYCOL

REFERENCE TO PRIOR APPLICATIONS

This application claims the benefit of European Patent Application No. 07114306.9, filed on Aug. 14, 2007, which is incorporated herein by reference in its entirety.

FIELD OF THE INVENTION

The present invention relates to a process for the preparation of an alkylene glycol from an alkene.

BACKGROUND OF THE INVENTION

Monoethylene glycol is used as a raw material in the manufacture of polyester fibres, polyethylene terephthalate (PET) plastics and resins. It is also incorporated into automobile antifreeze liquids.

Monoethylene glycol is typically prepared from ethylene oxide (EO), which is in turn prepared from ethylene. Ethylene and oxygen are passed over a silver-based catalyst, typically at pressures of 10-30 bar and temperatures of 200-300° C., producing a product stream typically comprising ethylene oxide, carbon dioxide, ethylene, oxygen and water. The amount of ethylene oxide in the product stream is usually between about 0.5 and 10 mole percent. The product stream is supplied to an ethylene oxide absorber and the ethylene oxide is absorbed by a recirculating solvent stream containing mostly water. The ethylene oxide-depleted stream is partially or entirely supplied to a carbon dioxide absorption column wherein the carbon dioxide is at least partially absorbed by a recirculating absorbent stream. Gases that are not absorbed by the recirculating absorbent stream are recombined with any gases bypassing the carbon dioxide absorption column and are recycled to the ethylene oxide reactor.

The solvent stream leaving the ethylene oxide absorber is referred to as fat absorbent. The fat absorbent is supplied to an ethylene oxide stripper, wherein ethylene oxide is removed from the fat absorbent as a vapour stream. The ethylene oxide-depleted solvent stream is referred to as lean absorbent and is recirculated to the ethylene oxide absorber to absorb further ethylene oxide.

The ethylene oxide obtained from the ethylene oxide stripper can be purified for storage and sale or can be further reacted to provide ethylene glycol. In one well-known process, ethylene oxide is reacted with a large excess of water in a non-catalytic process. This reaction typically produces a glycol product stream consisting of almost 90 weight percent monoethylene glycol, the remainder being predominantly diethylene glycol, some triethylene glycol and a small amount of higher homologues. In another well-known process, ethylene oxide is catalytically reacted with carbon dioxide to produce ethylene carbonate. The ethylene carbonate is subsequently hydrolysed to provide ethylene glycol. Reaction via ethylene carbonate significantly improves the selectivity of ethylene oxide conversion to monoethylene glycol.

Efforts have been made to simplify the process for obtaining ethylene glycol from ethylene, reducing the equipment that is required and reducing the energy consumption. GB 2 107 712 describes a process for preparing monoethylene glycol wherein the gases from the ethylene oxide reactor are supplied directly to a reactor wherein ethylene oxide is converted to ethylene carbonate or to a mixture of ethylene glycol and ethylene carbonate. EP 776 890 describes a process wherein the gases from the ethylene oxide reactor are supplied to an absorber wherein the absorbing solution mainly contains ethylene carbonate and ethylene glycol. The ethylene oxide in the absorbing solution is supplied to a carboxylation reactor and allowed to react with carbon dioxide in the presence of a carboxylation catalyst. The ethylene carbonate in the absorbing solution is subsequently supplied with the addition of water to a hydrolysis reactor and subjected to hydrolysis in the presence of a hydrolysis catalyst.

The present inventors have sought to further improve the manufacture of alkylene glycol from an alkene. In particular, the present inventors have sought to provide a process that reduces the cost and complexity of the plant whilst ensuring high selectivity.

SUMMARY OF THE INVENTION

Accordingly, the present invention provides a process for the preparation of an alkylene glycol from an alkene comprising steps of:

(a) reacting the alkene with oxygen in the presence of a catalyst in a reactor to produce a gas composition comprising alkylene oxide, alkene, oxygen, carbon dioxide and water vapour, and removing contaminants from the gas composition;

(b) supplying the gas composition from (a) to an alkylene oxide absorber comprising a column of vertically stacked trays or comprising a packed column, supplying lean absorbent to the alkylene oxide absorber, contacting the gas composition with lean absorbent in the alkylene oxide absorber in the presence of one or more catalysts that promote carboxylation and hydrolysis, and withdrawing fat absorbent from the alkylene oxide absorber, wherein the lean absorbent comprises at least 20 wt % water, and wherein at least 50% of the alkylene oxide entering the alkylene oxide absorber is converted in the alkylene oxide absorber;

(c) optionally supplying a portion or all of the fat absorbent from step (b) to one or more finishing reactors and withdrawing a product stream from the one or more finishing reactors, wherein at least 90% of alkylene oxide and alkylene carbonate entering the one or more finishing reactors is converted to alkylene glycol in the one or more finishing reactors;

(d) optionally supplying the fat absorbent from step (b) or a product stream from at least one of the one or more finishing reactors in step (c) to a flash vessel or to a light ends stripper and removing light ends;

(e) supplying the fat absorbent from step (b) or (d), or the product stream from step (c) or (d) to a dehydrator, removing water and providing a dehydrated product stream; and (f) purifying the dehydrated product stream from step (e) and providing a purified alkylene glycol product stream.

In the process of the invention, the alkylene oxide absorber acts both as an absorber, absorbing alkylene oxide from the gas composition, and as reactor, converting alkylene oxide to alkylene carbonate and/or alkylene glycol. At least 50% of the alkylene oxide entering the alkylene oxide absorber is converted to alkylene carbonate and/or alkylene glycol. In one embodiment the process also uses one or more finishing reactors that provide further conversion of alkylene oxide and alkylene carbonate that are not converted in the alkylene oxide absorber.

In the process of the present invention, carboxylation and hydrolysis occurs in an alkylene oxide absorber comprising a column of vertically stacked trays or comprising a packed column. Such absorbers are conventionally used for mass transfer processes rather than chemical reactions. In the processes disclosed in GB 2 107 712 the gases from the ethylene oxide reactor pass directly to a carboxylation reactor or a hydrolysis reactor and the nature of this reactor is unspecified. The present inventors have surprisingly demonstrated that an alkylene oxide absorber comprising a column of vertically stacked trays or comprising a packed column can perform the dual functions of absorption and reaction.

The process of the present invention balances the requirements of achieving high conversion and selectivity, whilst reducing the equipment used to carry out the process. In contrast to the process disclosed in EP 776 890, which uses an absorber, a carboxylation reactor and a hydrolysis reactor, the process of the present invention achieves significant conversion of alkylene oxide in the absorber, and thereby reduces the requirement for reactor vessels. The process of the invention optionally uses finishing reactors but these can typically be significantly smaller than reactors in prior art processes wherein the majority of carboxylation and hydrolysis occurs.

DETAILED DESCRIPTION OF THE INVENTION

Figure 1:
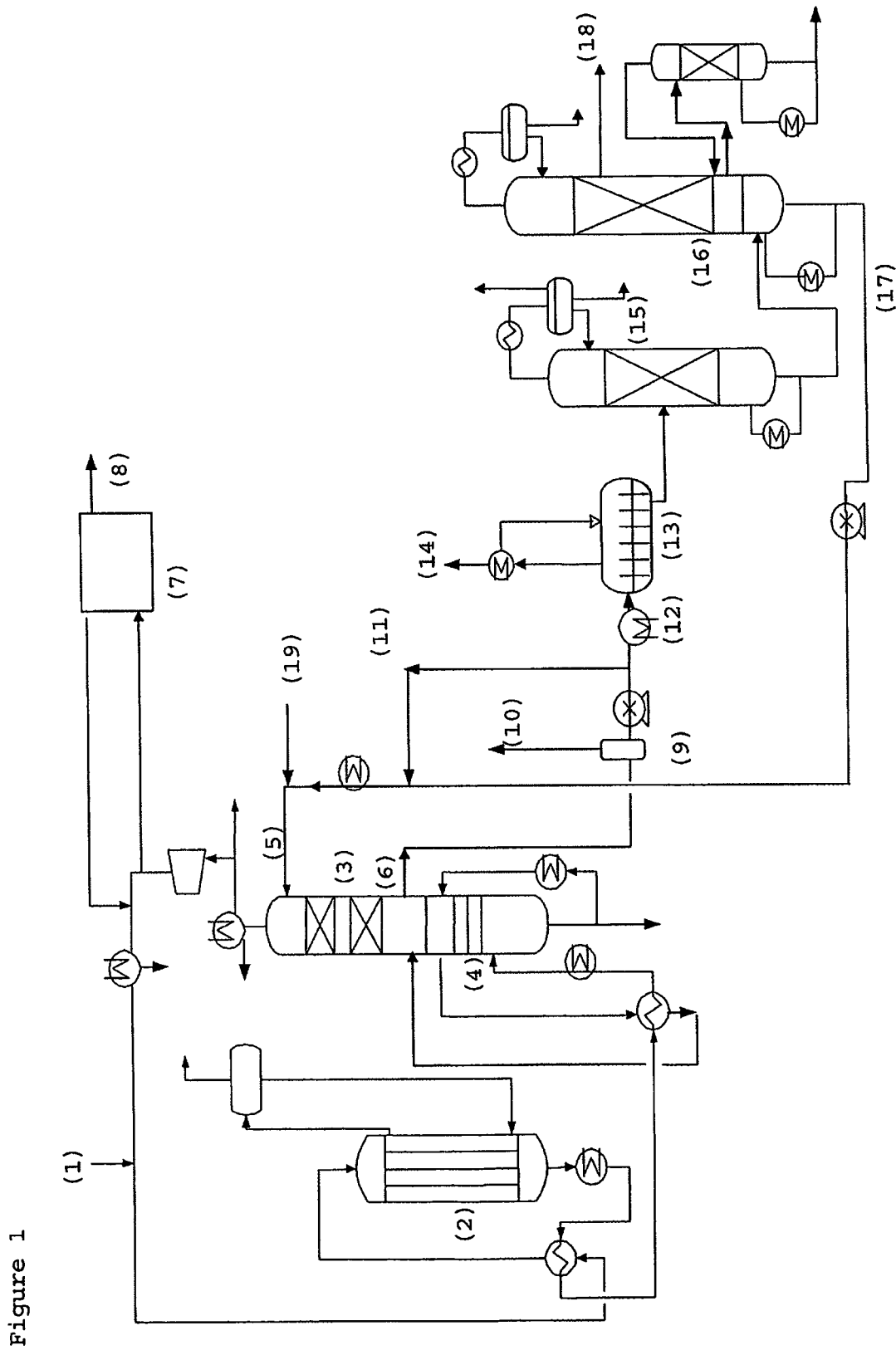
FIG. 1 is a schematic diagram showing a process according to an embodiment of the invention.

The present invention provides a process for the preparation of an alkylene glycol from an alkene:

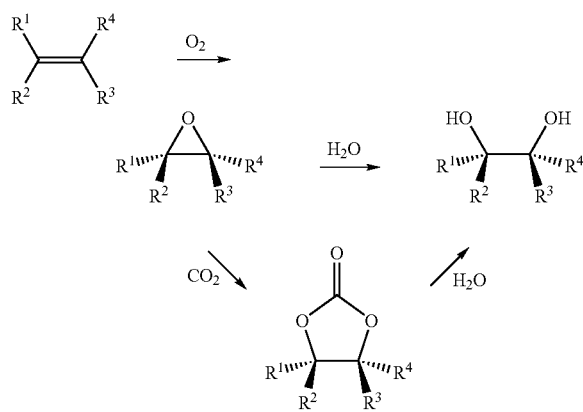

$R^1$, $R^2$, $R^3$ and $R^4$ are preferably chosen from hydrogen or an optionally substituted alkyl group having from 1 to 6 carbon atoms, more preferably from 1 to 3 carbon atoms. As substituents, moieties such as hydroxy groups may be present. Preferably, $R^1$, $R^2$ and $R^3$ represent hydrogen atoms and $R^4$ represents hydrogen or a non-substituted $C_1$-$C_3$-alkyl group and, more preferably, $R^1$, $R^2$, $R^3$ and $R^4$ all represent hydrogen atoms.

Examples of suitable alkenes therefore include ethylene and propylene. In the present invention, the most preferred alkene is ethylene.

The alkene is reacted with oxygen in the presence of a catalyst in a reactor to produce a gas composition comprising alkylene oxide, alkene, oxygen, carbon dioxide and water vapour. The oxygen may be supplied as oxygen or as air, but is preferably supplied as oxygen. Ballast gas, for example methane or nitrogen, is typically supplied to allow operation at high oxygen levels without causing a flammable mixture. Moderator, e.g. monochloroethane or dichloroethane, may be supplied for ethylene oxide catalyst performance control. The alkene, oxygen, ballast gas and moderator are preferably supplied to recycle gas that is supplied to the alkylene oxide reactor from the alkylene oxide absorber (optionally via a carbon dioxide absorption column).

The alkylene oxide reactor is typically a multitubular, fixed bed reactor. The catalyst is preferably finely dispersed silver and optionally promoter metals on a support material, for example, alumina. The reaction is preferably carried out at pressures of greater than 1 MPa and less than 3 MPa and temperatures of greater than 200° C. and less than 300° C. The gas composition from the alkylene oxide reactor is preferably cooled in one or more coolers, preferably with generation of steam at one or more temperature levels.

Contaminants are removed from the gas composition before it is supplied to the alkylene oxide absorber. Possible contaminants include acids, esters, aldehydes, acetals and organic halides. A preferred method of removing contaminants is quenching, preferably by contacting the gas composition with a cooled recirculating aqueous solution. Quenching is preferably carried out in the same vessel as the alkylene oxide absorber; the quench section is preferably below the vertically stacked trays or the packing of the alkylene oxide absorber. A portion of the recirculating aqueous solution may be withdrawn as a bleed stream from the quench section, and any alkylene oxide in the bleed stream may be recovered by conventional methods. After quenching, the gas composition may be reheated before it is supplied to the alkylene oxide absorber, preferably by heat integration with the hot gas composition emerging from the alkylene oxide reactor.

The gas composition from the oxidation step (a) is supplied to an alkylene oxide absorber comprising a column of vertically stacked trays or comprising a packed column. The trays or the packed column provide a surface area for the absorbent and gas composition to come into contact, facilitating mass transfer between the two phases. Additionally, trays provide considerable liquid volume in which the liquid phase reaction can occur. In the embodiment wherein the alkylene oxide absorber comprises a series of vertically stacked trays, gases can pass upwards through the trays and liquid can flow downwards from tray to tray. Preferably, the column comprises at least 20 trays, more preferably at least 30 trays. Preferably, the column comprises less than 100 trays, more preferably less than 70 trays. More trays increase the absorption ability and reaction volume of the column, but adding additional trays increases expense. In the embodiment wherein the alkylene oxide absorber comprises a packed column, conventional packing such as structured packing, random packing and catalytic distillation internals may be used.

The gas composition from the oxidation step (a) is preferably supplied at the bottom of the alkylene oxide absorber. If the alkylene oxide absorber comprises a column of vertically stacked trays, the gas composition is preferably supplied below the bottom tray in the column. If the alkylene oxide absorber comprises a packed column, the gas composition is preferably supplied below the packing material.

Lean absorbent is supplied to the alkylene oxide absorber and contacted with the gas composition in the alkylene oxide absorber and fat absorbent (comprising components absorbed from the gas composition including alkylene carbonate and alkylene glycol) is withdrawn from the alkylene oxide absorber. In one embodiment, the lean absorbent is supplied at the top of the alkylene oxide absorber. If the alkylene oxide absorber comprises a column of vertically stacked trays, the lean absorbent is preferably supplied to the uppermost tray in the absorption column. If the alkylene oxide absorber comprises a packed column, the lean absorbent is preferably supplied above the packing material. In another embodiment, the lean absorbent is supplied such that there are trays or packing above the point at which the lean absorbent is supplied to the alkylene oxide absorber. In this embodiment, cold water or additional lean absorbent that has been cooled can be supplied at the top of the alkylene oxide absorber to absorb alkylene oxide or contaminants in the top of the alkylene oxide absorber.

The lean absorbent comprises at least 20 wt % water. The water that is present in the lean absorbent is used in the hydrolysis of alkylene oxide and alkylene carbonate that occurs in the alkylene oxide absorber. If the lean absorbent comprises less than 20 wt % water, then less hydrolysis is likely to occur and the conversion to alkylene glycol may be lower. Also, depending on the nature of the one or more catalysts that promote carboxylation and hydrolysis, catalyst performance may suffer if the lean absorbent comprises less than 20 wt % water. Preferably, the lean absorbent comprises at least 30 wt % water, more preferably at least 40 wt % water. Preferably, the lean absorbent comprises less than 80 wt % water. More than 80 wt % water in the lean absorbent may still provide good selectivity and catalyst performance, but higher quantities of water require additional water removal, with associated energy and equipment costs. The lean absorbent may also comprise alkylene glycol and alkylene carbonate.

The gas composition is contacted with lean absorbent in the alkylene oxide absorber in the presence of one or more catalysts that promote carboxylation and hydrolysis. If this occurs in the presence of only one catalyst, then the catalyst must promote carboxylation and hydrolysis. If this occurs in the presence of two or more catalysts, then each catalyst can promote carboxylation or hydrolysis or can promote both reactions (provided that at least one catalyst promotes carboxylation and at least one catalyst promotes hydrolysis). In a preferred embodiment, the gas composition is contacted with lean absorbent in the presence of at least two catalysts including a first catalyst that promotes carboxylation and a second catalyst that promotes hydrolysis.

In one embodiment of the invention, the one or more catalysts that promote carboxylation and hydrolysis is/are homogeneous, and the lean absorbent comprises the one or more catalysts. Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenyl-propylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Homogeneous catalysts that are known to promote hydrolysis include basic alkali metal salts such as potassium carbonate, potassium hydroxide and potassium bicarbonate, or alkali metal metalates such as potassium molybdate. Preferred homogeneous catalyst systems include a combination of potassium iodide and potassium carbonate, and a combination of potassium iodide and potassium molybdate.

In another embodiment of the invention, the one or more catalysts that promote carboxylation and hydrolysis is/are heterogeneous and the heterogeneous catalyst(s) are contained in the vertically stacked trays or in the packing of a packed column. Heterogeneous catalysts that promote carboxylation include quaternary ammonium and quaternary phosphonium halides immobilized on silica, quaternary ammonium and quaternary phosphonium halides bound to insoluble polystyrene beads, and metal salts such as zinc salts immobilised on solid supports containing quaternary ammonium or quaternary phosphonium groups, such as ion exchange resins containing quaternary ammonium or quaternary phosphonium groups. Heterogeneous catalysts that promote hydrolysis include metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups.

In the embodiment wherein the gas composition is contacted with lean absorbent in the presence of at least two catalysts including a first catalyst that promotes carboxylation and a second catalyst that promotes hydrolysis, the ratio of first catalyst to second catalyst can be adjusted in order to vary the amount of carbon dioxide that is consumed or released in the alkylene oxide absorber. Preferably, the gases from the alkylene oxide absorber are partially or entirely supplied to a carbon dioxide absorption column wherein the carbon dioxide is at least partially absorbed by a recirculating absorbent stream. By controlling the amount of carbon dioxide that is consumed or released in the alkylene oxide absorber, the capacity and cost of a carbon dioxide absorber column can be reduced.

The temperature in the alkylene oxide absorber is preferably from 50° C. to 160° C., preferably from 80° C. to 150° C. This is higher than the temperature in an absorber in a conventional process and is required to promote the carboxylation and hydrolysis reactions. Temperature higher than 160° C. is not preferred as this may reduce the selectivity of the alkylene oxide conversion to alkylene glycol. Both the gas composition from the step (a) and the lean absorbent are preferably supplied to the alkylene oxide absorber at temperatures in the range from 50° C. to 160° C.

The pressure in the alkylene oxide absorber is from 1 to 4 MPa, preferably from 2 to 3 MPa. The preferred pressure is a compromise between lower pressures that require less expensive equipment (e.g. equipment having thinner walls) and higher pressures that increase absorption and reduce the volumetric flow of the gas, thereby reducing the size of equipment and piping.

At least 50% of the alkylene oxide entering the alkylene oxide absorber is converted in the alkylene oxide absorber. The alkylene oxide may undergo carboxylation, providing alkylene carbonate. The alkylene oxide may undergo hydrolysis, providing alkylene glycol. Additionally, the alkylene carbonate that is produced from the alkylene oxide may undergo hydrolysis, providing alkylene glycol. Preferably, at least 60% of the alkylene oxide entering the alkylene oxide absorber is converted in the alkylene oxide absorber, more preferably at least 70%.

The gas composition from step (a) that is supplied to the alkylene oxide absorber comprises carbon dioxide. It is possible that the gas composition may contain insufficient carbon dioxide to achieve desired levels of carboxylation. This is likely to be the case when using a fresh batch of catalyst in step (a). An additional source of carbon dioxide is preferably supplied to the alkylene oxide absorber, e.g. recycle carbon dioxide from a finishing reactor, carbon dioxide from a carbon dioxide recovery unit or, at start-up, carbon dioxide from an external source. The ratio of the total amount of carbon dioxide supplied to the alkylene oxide absorber to the amount of alkylene oxide supplied to the alkylene oxide absorber is preferably between 5:1 and 1:3, more preferably between 3:1 and 4:5. A higher quantity of carbon dioxide improves the selectivity of the process because most alkylene oxide reacts with carbon dioxide to alkylene carbonate, which is subsequently hydrolysed to alkylene glycol and there is less opportunity for reaction between alkylene oxide and alkylene glycol to produce higher glycols. However, a higher quantity of carbon dioxide also requires either additional removal capacity for carbon dioxide in the process, which can be costly, or operating the alkylene oxide catalyst at higher carbon dioxide concentration which adversely affects the catalyst performance.

Gases that are not absorbed in the alkylene oxide absorber are preferably partially or entirely supplied to a carbon dioxide absorption column wherein the carbon dioxide is at least partially absorbed by a recirculating absorbent stream. Gases that are not absorbed by the recirculating absorbent stream are preferably recombined with any gases bypassing the carbon dioxide absorption column and are recycled to the alkylene oxide reactor. Preferably, the gases are cooled prior to recycle to the alkylene oxide reactor in order to reduce the water content. This is preferred because the performance of the catalyst in the alkylene oxide reactor may be detrimentally affected by an excess of water. The water removed from the gas stream can optionally be recirculated to the alkylene oxide absorber.

If the one or more catalysts that promote carboxylation and hydrolysis include a halogen-containing catalyst (e.g. an alkali metal halide, a halogenated organic phosphonium or ammonium salt or a quaternary ammonium or quaternary phosphonium halide immobilized on a solid support), then gases that are recycled from the alkylene oxide absorber to the alkylene oxide reactor may comprise halide-containing impurities such as iodide-containing impurities or bromide-containing impurities. It is possible that the catalyst in the alkylene oxide reactor may be detrimentally affected by these impurities. Therefore, in this embodiment, it is preferred that gases that are recycled from the alkylene oxide absorber to the alkylene oxide reactor are contacted with a purification absorbent capable of reducing the quantity of halide-containing impurities (especially iodide-containing impurities or bromide-containing impurities) prior to contacting the catalyst in the alkylene oxide reactor. The purification absorbent may be located within the reactor tubes of the alkylene oxide reactor, within the alkylene oxide reactor upstream from the reactor tubes or in a separate reactor upstream from the alkylene oxide reactor.

The purification absorbent may suitably comprise a metal having an atomic number of 22 through 48 or 82, in particular 22 through 30.

In an embodiment, the purification absorbent comprises one or more metals selected from cobalt, chromium, copper, manganese, nickel, and zinc, in particular the one or more metals are selected from copper, nickel and zinc, more in particular the one or more metals comprise copper. Suitably, the purification absorbent comprises copper and one or more metals having an atomic number of 22 through 48. The purification absorbent may comprise copper and one or more metals selected from manganese, chromium, zinc, and combinations thereof. The purification absorbent may comprise copper and zinc. The metal may be present in reduced or oxide form, preferably as an oxide. The purification absorbent may also contain a support material. The support material may be selected from alumina, titania, silica, activated carbon or mixtures thereof. Preferably, the support material may be alumina, in particular alpha-alumina.

In an embodiment, the purification absorbent may comprise silver, an alkali or alkaline earth metal component, and a support material, as described herein. The support material may be, for example, a high surface area support material (having a surface area of more than 20 $m^2/g$), or a low surface area support material (having a surface area of less than 1 $m^2/g$).

In an embodiment, the purification absorbent may comprise an alkali metal carbonate or an alkaline earth metal carbonate. Suitably, the alkali metal may include lithium, sodium, potassium, rubidium, cesium, and mixtures thereof, in particular sodium, potassium and cesium. Suitably, the alkaline earth metal may include magnesium, calcium, strontium, barium, and mixtures thereof, in particular magnesium and calcium. Suitably, mixtures of alkali and alkaline earth metals may also be used. The purification absorbent may also contain a support material, as described herein. The support material may have a surface area in the range of from 0.1 to 300 $m^2/g$, relative to the weight of the support material, for example 0.5, 1, 10, 20, 50, 100, 150, 200, or 250 $m^2/g$, relative to the weight of the support material.

Fat absorbent is withdrawn from the alkylene oxide absorber, preferably by withdrawing liquid from the bottom of the alkylene oxide absorber, i.e. below the vertically stacked trays or packing.

In one embodiment of the invention, a portion or all of the fat absorbent from step (b) is supplied to one or more finishing reactors. Supply to one or more finishing reactors is preferred if a significant quantity (e.g. at least 1%) of alkylene oxide or alkylene carbonate is not converted to alkylene glycol in the alkylene oxide absorber. Conversely, if the majority (e.g. greater than 90%) of alkylene oxide and alkylene carbonate is converted to alkylene glycol in the alkylene oxide absorber, then one or more finishing reactors may not be required and the equipment used in the process is thereby reduced. To maximise conversion of alkylene oxide in the alkylene oxide absorber, spraying nozzles can be employed in the sump (bottom section) of the alkylene oxide absorber, to disperse carbon dioxide and promote carboxylation.

At least 90% of alkylene oxide and alkylene carbonate entering the one or more finishing reactors is converted to alkylene glycol in the one or more finishing reactors. This means that if there is one finishing reactor, at least 90% of alkylene oxide and alkylene carbonate entering the finishing reactor is converted to alkylene glycol in the finishing reactor, and if there is more than one finishing reactor, at least 90% of alkylene oxide and alkylene carbonate entering the first finishing reactor is converted to alkylene glycol before leaving the final finishing reactor. Preferably, at least 95% of alkylene oxide and alkylene carbonate entering the one or more finishing reactors is converted to alkylene glycol in the one or more finishing reactors, more preferably at least 98%.

In one embodiment of the invention, all of the fat absorbent is supplied to at least one of the one or more finishing reactors. In another embodiment of the invention, a portion of the fat absorbent is supplied to at least one of the one or more finishing reactors. Preferably, 10-90 wt % of the fat absorbent is supplied to at least one of the one or more finishing reactors, most preferably 30-70 wt % is supplied to at least one of the one or more finishing reactors. Preferably, the portion of the fat absorbent that is supplied to at least one of the one or more finishing reactors is pre-heated prior to supply to at least one of the one or more finishing reactors. Preferably, the portion of the fat absorbent is pre-heated to a temperature in the range 100-200° C., preferably about 150° C., in a heat exchanger.

If there is more than one finishing reactor it is preferred that the finishing reactors are connected in series, i.e. the fat absorbent must pass through each finishing reactor sequentially.

In one embodiment of the invention, at least one of the one or more finishing reactors is a baffled reactor, wherein the baffled reactor has at least four compartments, the compartments are formed by internal baffles and the internal baffles provide a sinuous route for reaction fluid through the reactor. Optionally, steam is injected into the baffled reactor.

Carbon dioxide may be produced in the one or more finishing reactors and is preferably separated from the product stream as it leaves the one or more finishing reactors and recycled.

The temperature in the one or more finishing reactors is typically from 100 to 200° C., preferably from 100 to 180° C. The pressure in the one or more finishing reactors is typically from 0.1 to 3 MPa.

The fat absorbent from step (b) or a product stream from at least one of the one or more finishing reactors in step (c) is optionally supplied to a flash vessel or to a light ends stripper. Light ends are removed in the flash vessel or in the light ends stripper. (Light ends are gases such as the alkene, and also ballast gases such as methane, that are present in the gas composition resulting from (a) and are absorbed into the absorbent in step (b).)

A flash vessel may be located directly after the alkylene oxide absorber so the fat absorbent passes directly from step (b) to the flash vessel. When there is at least one finishing reactor, a flash vessel may be located after all of the one or more finishing reactors so that the product stream passes from step (c) to the flash vessel. When there is more than one finishing reactor, a flash vessel may be located between the finishing reactors such that the fat absorbent passes from step (b) to at least one finishing reactor, then the product stream passes to the flash vessel and then the stream from the flash vessel passes to at least another finishing reactor.

The flash can be at pressure from 0.01 to 2 MPa, preferably from 0.1 to 1 MPa, most preferably from 0.1 to 0.5 MPa.

A light ends stripper can be used as an alternative to the flash vessel. In the light ends stripper, carbon dioxide gas is dispersed through the fat absorbent from step (b) or the product stream from at least one of the one or more finishing reactors in step (c), and the carbon dioxide effectively strips the light ends from the liquid. This is similar to supplying carbon dioxide via spraying nozzles to the sump (bottom section) of the alkylene oxide absorber, but it takes place in a separate vessel. The carbon dioxide supplied to the light ends stripper is preferably at a pressure higher than the pressure in the alkylene oxide absorber so that gases leaving the light ends stripper can be supplied to the alkylene oxide absorber without compression.

The light ends from the flash vessel or the light ends stripper are preferably recirculated to the alkylene oxide absorber; they may be combined with the gas composition from step (a) before it is supplied to the alkylene oxide absorber, or the light ends may be supplied at the bottom of the alkylene oxide absorber. Recirculating the light ends to the alkylene oxide absorber increases the efficiency of the process because light ends, comprising alkene, are recovered and are not lost when carbon dioxide is removed from the process in a carbon dioxide bleed stream.

Preferably, a portion of fat absorbent from step (b) or (d), or a portion of the product stream from step (c) or (d) is recycled to the alkylene oxide absorber as lean absorbent.

Fat absorbent from step (b) or (d), or the product stream from step (c) or (d) is supplied to a dehydrator. The stream that is supplied to the dehydrator preferably comprises very little alkylene oxide or alkylene carbonate, i.e. most of the alkylene oxide or alkylene carbonate has been converted to alkylene glycol prior to supply to the dehydrator column, either in the alkylene oxide absorber or in a finishing reactor. Preferably, the molar ratio of alkylene glycol to alkylene oxide and alkylene carbonate (combined) in the stream supplied to the dehydrator column is greater than 90:10, more preferably greater than 95:5, most preferably greater than 99:1.

The dehydrator is preferably one or more columns, including at least one vacuum column, preferably operating at a pressure of less than 0.05 MPa, more preferably less than 0.025 MPa and most preferably about 0.0125 MPa.

The dehydrated product stream from step (e) is purified to remove impurities and provide a purified alkylene glycol product stream. If the one or more catalysts are homogeneous catalysts, it will be necessary to separate the one or more catalysts from the dehydrated product stream, preferably in a flash vessel. The one or more homogeneous catalysts are preferably recombined with the lean absorbent and supplied to the alkylene oxide absorber.

FIG. 1 shows a preferred embodiment of the process of the invention. Ethylene, oxygen, methane and moderator (e.g. monochloroethane) are supplied to the recycle gas at (1). In the ethylene oxide reactor (2), the ethylene and oxygen react, providing a gas composition comprising ethylene, oxygen, methane, ethylene oxide, moderator and carbon dioxide, which is cooled and supplied to the quench (4), below the bottom tray of the quench section. The quenched gas is reheated and fed to the ethylene oxide absorber column (3) below the bottom tray or below the packing material. Optionally, additional carbon dioxide from the carbon dioxide recovery section (8) or finishing reactor (14) may also be supplied to the ethylene oxide absorber (3) or may be mixed with the gases before supply to the ethylene oxide absorber. Lean absorbent comprising at least 20 wt % water, a homogeneous hydrolysis catalyst and a homogeneous carboxylation catalyst is supplied (5) at the top of the ethylene oxide absorber (3). In the ethylene oxide absorber, ethylene oxide and carbon dioxide are absorbed into the lean absorbent and react to provide ethylene carbonate. The ethylene carbonate and ethylene oxide react with water to provide ethylene glycol. The gases that are not absorbed in ethylene oxide absorber (3) are partially or entirely supplied to carbon dioxide recovery section (7) where carbon dioxide is removed from the gas. The recovered carbon dioxide stream (8) can partially or entirely be recirculated to the ethylene oxide absorber (3), directly or by mixing with the gas feed. The gas from the ethylene oxide absorber column (3), the gas from carbon dioxide recovery section (7) and the recombined gas stream fed to the reactor can be cooled to reduce the water content. The liquid knocked out of the gas stream can optionally be recirculated to the ethylene oxide absorber column (3). Fat absorbent is withdrawn (6) from the ethylene oxide absorber bottom and is supplied to a flash vessel (9) where light ends are removed. The light ends stream (10) can be recirculated to the ethylene oxide absorber (3) directly or by mixing with the gas feed. The fat absorbent stream is split and one portion is fed to heat exchanger (12) and is subsequently supplied to a finishing reactor (13). In the finishing reactor (13), further reaction of ethylene carbonate to ethylene glycol and ethylene oxide to ethylene glycol occurs. The carbon dioxide gas released (14) can be recycled to the ethylene oxide absorber (3) directly, or by mixing with the ethylene oxide absorber feed, or can be totally or partially bled. The liquid product stream from the finishing reactor (13) is supplied to a dehydrator (15) where water is removed. The dehydrated product stream is withdrawn from the dehydrator (15) and supplied to the monoethylene glycol (MEG) purification column (16). A solution comprising the carboxylation and hydrolysis catalysts dissolved in glycols (17) is withdrawn from the bottom of the MEG purification column (16) and is recycled to the ethylene oxide absorber (3) as lean absorbent (5) after mixing with the absorbent flow that is not supplied to the finishing reactor (11). Monoethylene glycol product (18) is withdrawn from the MEG purification column top section. Make-up water (19) can be supplied to the lean absorbent.

Figure 2:
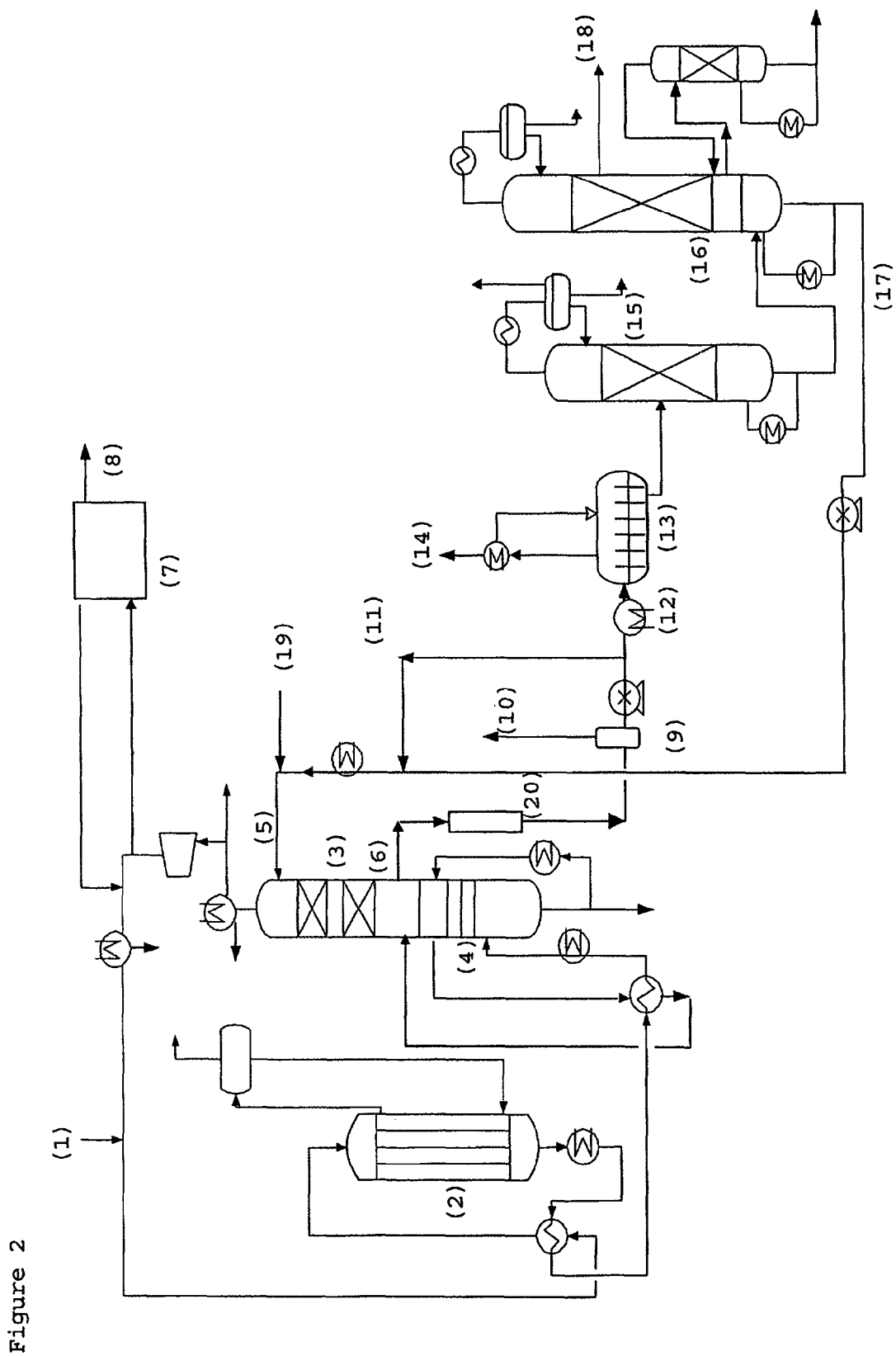
FIG. 2 is a schematic diagram showing a process according to another embodiment of the invention.

FIG. 2 shows an alternative preferred embodiment of the process of the invention where the fat absorbent stream (6) from the ethylene oxide absorber column (3) is supplied directly to a first finishing reactor (20) to convert all remaining ethylene oxide to ethylene carbonate and/or ethylene glycol before supply to the flash vessel (9). As in FIG. 1, after the flash vessel, the stream is split and one portion is fed to heat exchanger (12) and is subsequently supplied to a finishing reactor (13) wherein further reaction of ethylene carbonate to ethylene glycol and ethylene oxide to ethylene glycol occurs. In FIG. 2, the finishing reactor (13) is the second finishing reactor.

Figure 3:
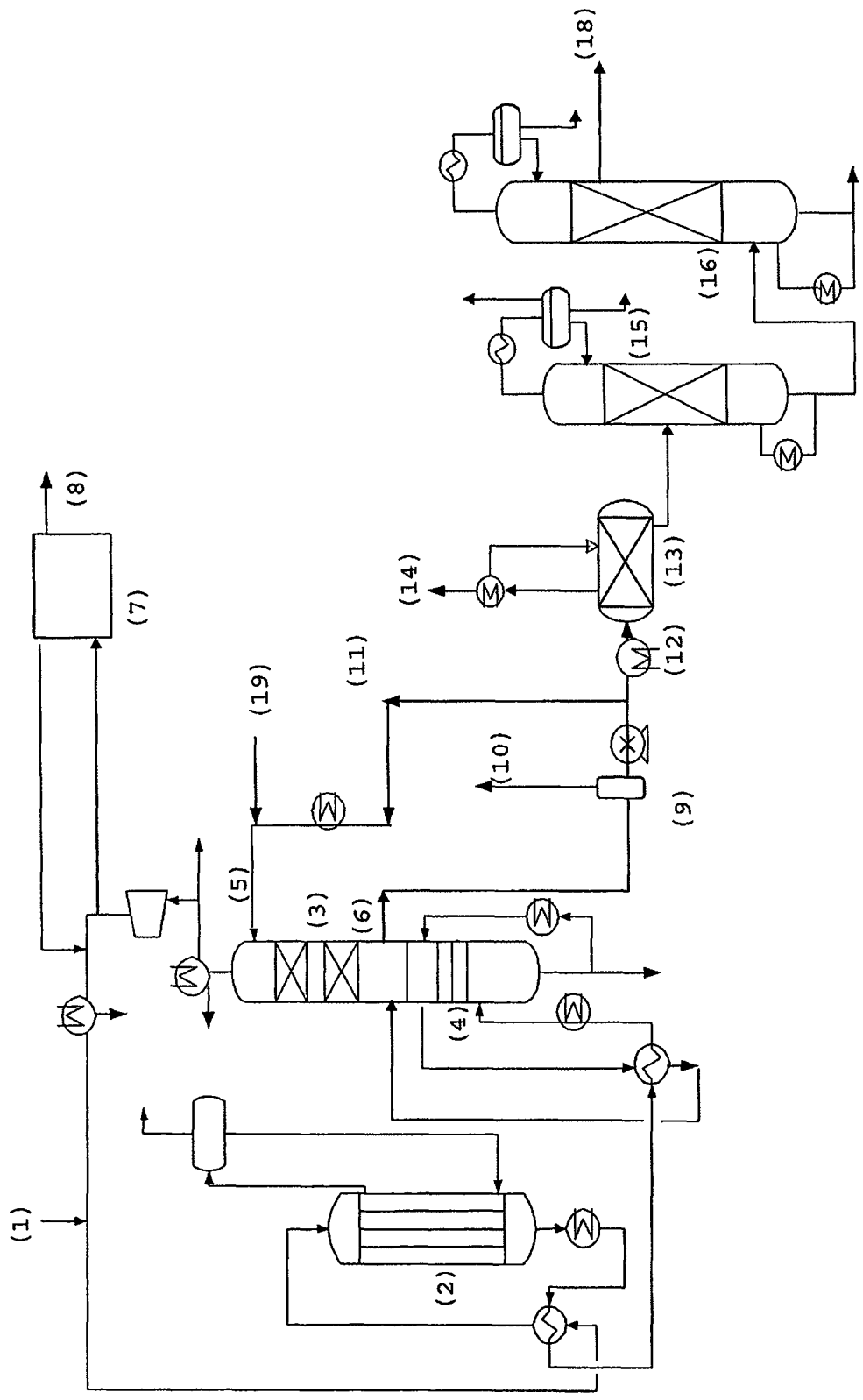
FIG. 3 is a schematic diagram showing a process according to another embodiment of the invention.

FIG. 3 shows yet another preferred embodiment of the process comprising a heterogeneous catalyst packing in the ethylene oxide absorber column (3) as well as a heterogeneous catalyst bed in the finishing reactor (13). In this embodiment, there is no catalyst recirculation flow needed from the bottom of MEG purification column (17).

Figure 4:
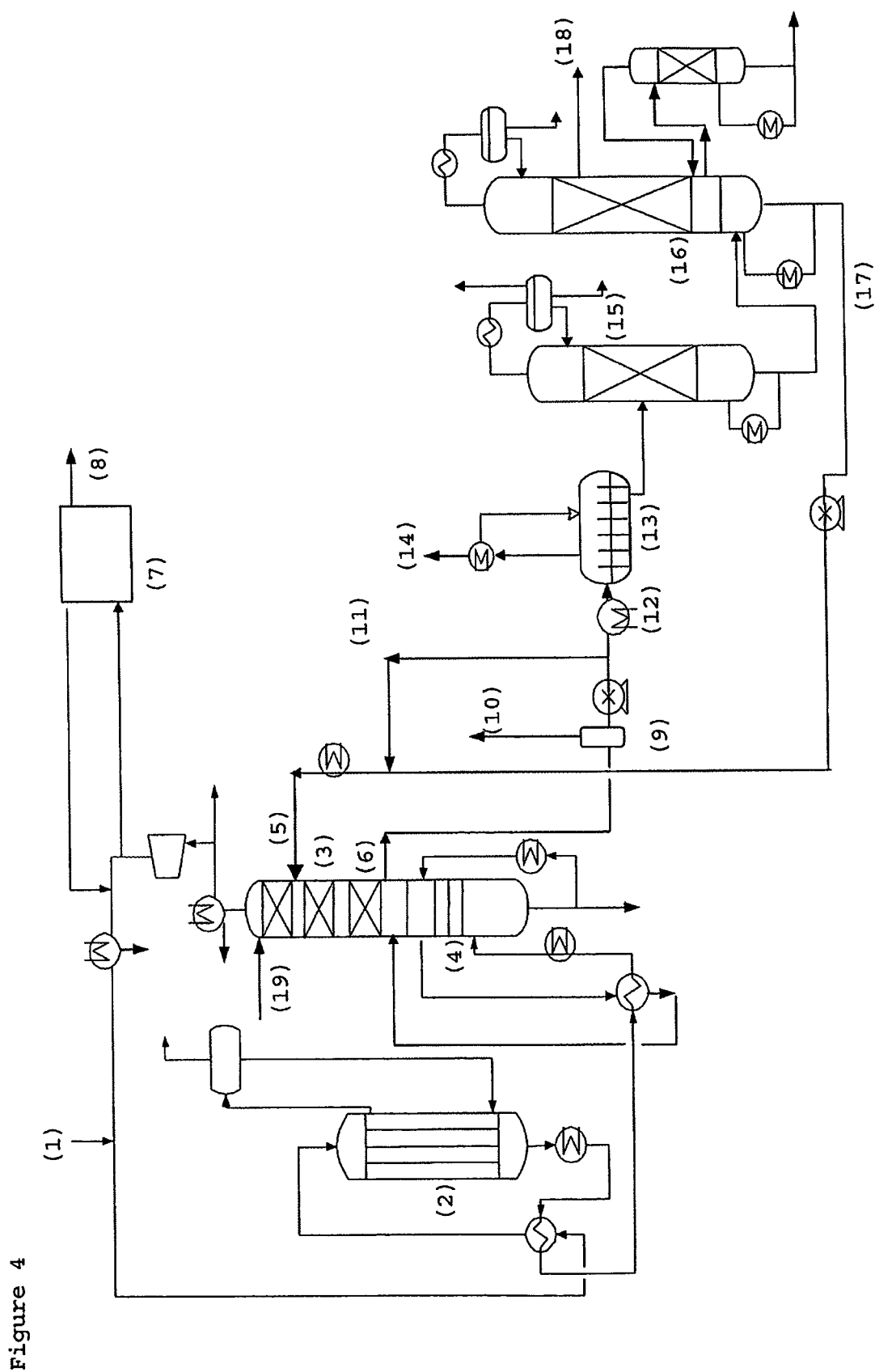
FIG. 4 is a schematic diagram showing a process according to another embodiment of the invention.

FIG. 4 shows an embodiment where packing or trays are present in ethylene oxide absorber column (3) above the point where lean absorbent enters the column. Cold water or absorbent can be fed to the column above this top packing or top trays to absorb remaining ethylene oxide and/or contaminants in the top of the ethylene oxide absorber.

Figure 5:
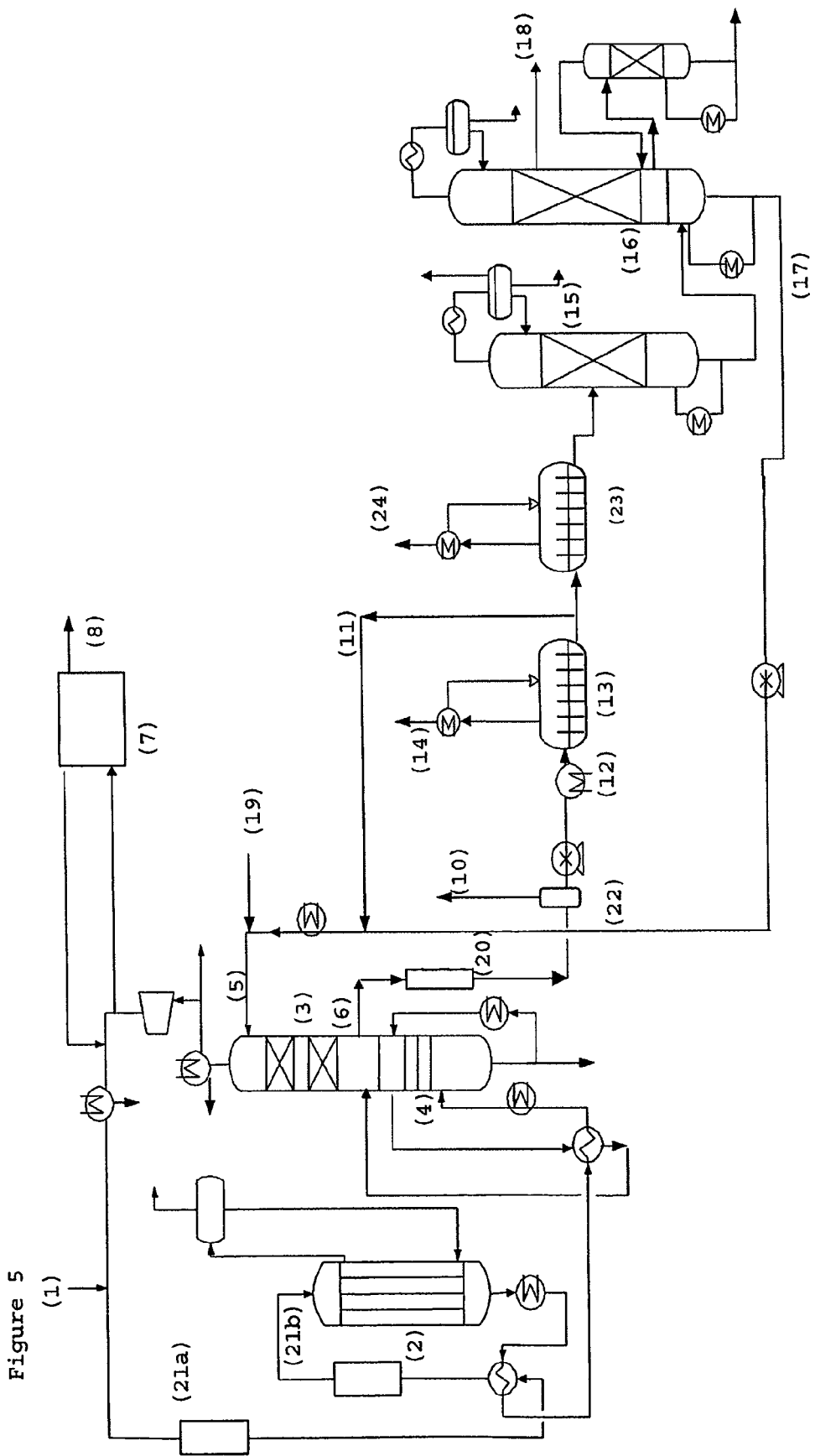
FIG. 5 is a schematic diagram showing a process according to another embodiment of the invention.

FIG. 5 shows an embodiment wherein the gas from the ethylene oxide absorber column (3), the gas from carbon dioxide recovery section (7) and the recombined gas stream fed to the reactor are led through a guard bed (21a or 21b), where traces of halogen containing impurities that can poison the EO catalyst in the EO reactor are removed. Depending on the optimal operating temperature of the guard bed, it can be located in the gas stream before (21a) or after (21b) heating the gas to EO reactor inlet temperature.

In this embodiment, the fat absorbent stream (6) from the ethylene oxide absorber column (3) is supplied directly to a first finishing reactor (20) to convert all remaining ethylene oxide to ethylene carbonate and/or ethylene glycol before supply to the light ends stripping vessel (22). Recycle carbon dioxide from second finishing reactor (14) and/or carbon dioxide recovery section (8) is fed as stripping gas to the light ends stripper (22). The gas stream of carbon dioxide and light ends (10) can be recirculated to the ethylene oxide absorber (3) directly or by mixing with the gas feed. The fat absorbent stream leaving the stripping vessel is fed to heat exchanger (12) and is subsequently supplied to a second finishing reactor (13). In the second finishing reactor (13), further reaction of ethylene carbonate to ethylene glycol and ethylene oxide to ethylene glycol occurs. The carbon dioxide gas released (14) is recycled to the light ends stripper (22). The reactor product of the secondary finishing reactor is split and one part is fed to third finishing reactor (23). The carbon dioxide released in this third finishing reactor is bled from the process (24). The liquid product stream from the third finishing reactor (23) is supplied to a dehydrator (15) where water is removed. The dehydrated product stream is withdrawn from the dehydrator (15) and supplied to the monoethylene glycol (MEG) purification column (16). A solution comprising the carboxylation and hydrolysis catalysts dissolved in glycols (17) is withdrawn from the bottom of the MEG purification column (16) and is recycled to the ethylene oxide absorber (3) as lean absorbent (5) after mixing with the reactor product of the secondary finishing reactor absorbent flow that is not supplied to the third finishing reactor (11).

Figure 6:
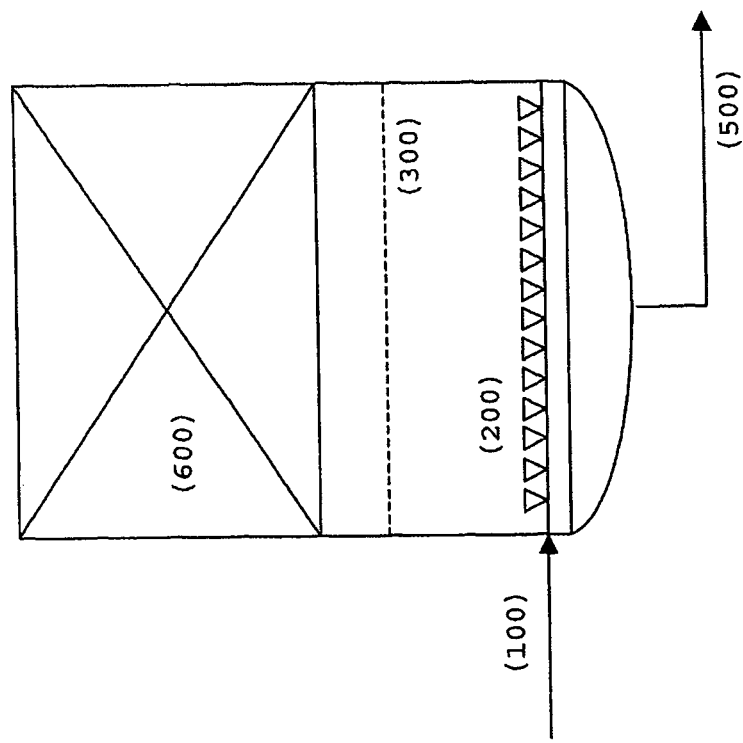
FIG. 6 is a schematic diagram showing an embodiment of the bottom or sump of the alkylene oxide absorber column.

FIG. 6 describes an embodiment of the bottom or sump of the ethylene oxide absorber column, where carbon dioxide gas (100) is supplied to the liquid though nozzles (200). The liquid level (300) is maintained well below the bottom tray or below the bottom of the column packing (600). Fat absorbent (500) leaves at the bottom.

What is claimed is:

1. A process for the preparation of an alkylene glycol from an alkene comprising steps of:
   (a) reacting the alkene with oxygen in the presence of an alkylene oxide catalyst in an alkylene oxide reactor to produce a gas composition comprising alkylene oxide, alkene, oxygen, carbon dioxide and water vapor, and removing contaminants from the gas composition;
   (b) supplying the gas composition from step (a) to an alkylene oxide absorber comprising a column of vertically stacked trays or a packed column, supplying a lean absorbent comprising at least 20 wt % water and less than 80 wt % water to the alkylene oxide absorber, contacting the gas composition with the lean absorbent in the alkylene oxide absorber in the presence of one or more catalysts that promote carboxylation and hydrolysis, and withdrawing a fat absorbent that comprises at least one product selected from the group consisting of an alkylene carbonate and an alkylene glycol from the alkylene oxide absorber, wherein at least 50% of the alkylene oxide entering the alkylene oxide absorber is converted in the alkylene oxide absorber; and
   (c) supplying at least a portion of the fat absorbent to a dehydrator to produce a dehydrated product stream comprising alkylene glycol.

2. The process according to claim 1, wherein the one or more catalysts that promote carboxylation and hydrolysis are homogeneous.

3. The process according to claim 1, wherein the lean absorbent comprises the one or more catalysts.

4. The process according to claim 2, wherein the one or more catalysts comprise an alkali metal halide.

5. The process according to claim 1, wherein the one or more catalysts comprise potassium iodide and potassium carbonate.

6. The process according to claim 1, wherein the one or more catalysts comprise potassium iodide and potassium molybdate.

7. The process according to claim 1, wherein step (b) further comprises supplying an additional source of carbon dioxide to the alkylene oxide absorber.

8. The process according to claim 1, wherein step (b) further comprises supplying at least a portion of the gas composition that is not absorbed in the alkylene oxide absorber to a carbon dioxide absorption column.

9. The process according to claim 1, wherein step (c) further comprises supplying the portion of the fat absorbent to one or more finishing reactors prior to the portion being supplied to the dehydrator, and wherein at least 90% of the alkylene oxide and alkylene carbonate entering the one or more finishing reactors is converted to alkylene glycol in the one or more finishing reactors.

10. The process according to claim 1, wherein spraying nozzles are employed in a bottom section of the alkylene oxide absorber, to disperse carbon dioxide and promote carboxylation.

11. The process according to claim 9, wherein 10-90 wt % of the fat absorbent is pre-heated and then supplied to at least one of one or more finishing reactors.

12. The process according to claim 1, wherein step (c) further comprises supplying the portion of the fat absorbent to a flash vessel prior to the portion being supplied to the dehydrator, and wherein light ends are removed in the flash vessel and recirculated to the alkylene oxide absorber.

13. The process according to claim 1, wherein step (c) further comprises supplying the portion of the fat absorbent to a light ends stripper prior to the portion being supplied to the dehydrator, wherein light ends are removed in the light ends stripper by stripping with carbon dioxide, and wherein the light ends and carbon dioxide are recirculated to the alkylene oxide absorber.

14. The process according to claim 1, wherein at least a portion of the fat absorbent is recycled to the alkylene oxide absorber as lean absorbent.

15. A process for the preparation of ethylene glycol from ethylene comprising steps of:
   (a) reacting the ethylene with oxygen in the presence of an ethylene oxide catalyst in an ethylene oxide reactor to produce a gas composition comprising ethylene oxide, ethylene, oxygen, carbon dioxide and water vapor, and removing contaminants from the gas composition;
   (b) supplying the gas composition from step (a) to an ethylene oxide absorber comprising a column of vertically stacked trays or a packed column, supplying a lean absorbent comprising at least 20 wt % water and less than 80 wt % water to the ethylene oxide absorber, contacting the gas composition with the lean absorbent in the ethylene oxide absorber in the presence of one or more catalysts that promote carboxylation and hydrolysis, and withdrawing a fat absorbent that comprises at least one product selected from the group consisting of ethylene carbonate and ethylene glycol from the ethylene oxide absorber, wherein at least 50% of the ethylene oxide entering the ethylene oxide absorber is converted in the ethylene oxide absorber;
   (c) supplying at least a portion of the fat absorbent from step (b) to one or more finishing reactors and withdrawing a product stream comprising ethylene glycol from the one or more finishing reactors, wherein at least 90% of ethylene oxide and ethylene carbonate entering the one or more finishing reactors is converted to ethylene glycol in the one or more finishing reactors;
   (d) supplying the fat absorbent from step (b) or the product stream from at least one of the one or more finishing reactors in step (c) to a flash vessel or a light ends stripper and removing light ends;
   (e) supplying at least a portion of the fat absorbent from step (b) or (d), or at least a portion of the product stream from step (c) or (d), to a dehydrator to produce a dehydrated product stream comprising ethylene glycol; and
   (f) purifying the dehydrated product stream to produce a purified ethylene glycol product stream.

16. The process according to claim 15, wherein the one or more catalysts comprise potassium iodide and at least one selected from the group consisting of potassium carbonate and potassium bicarbonate.

17. The process according to claim 1 further comprising the step of:
   (d) purifying the dehydrated product stream to produce a purified alkylene glycol product stream.

* * * * *